(12) United States Patent
Park et al.

(10) Patent No.: US 6,888,019 B1
(45) Date of Patent: May 3, 2005

(54) METHOD OF PREPARING RHENIUM COMPLEX USING BOROHYDRIDE EXCHANGE RESIN

(75) Inventors: Sang Hyun Park, Taejon (KR); Kyung Bae Park, Taejon (KR); Sun Ju Choi, Taejon (KR)

(73) Assignee: Korea Atomic Energy Research Institute, Taejon (KR)

( * ) Notice: Subject to any disclaimer, the term of this patent is extended or adjusted under 35 U.S.C. 154(b) by 45 days.

(21) Appl. No.: 10/838,805

(22) Filed: May 4, 2004

(30) Foreign Application Priority Data

Feb. 25, 2004 (KR) ................................ 10-2004-0012732

(51) Int. Cl.[7] ......................... C07F 13/00; A61K 51/00
(52) U.S. Cl. ....................................... 556/45; 424/1.11
(58) Field of Search ............................ 556/45; 424/1.11

(56) References Cited

U.S. PATENT DOCUMENTS 5,955,053 A * 9/1999 Marzilli et al. ............ 424/1.11
5,986,074 A * 11/1999 Marzilli et al. ............... 534/14
6,437,103 B1 * 8/2002 Babich et al. ................. 534/14
2003/0194365 A1 * 10/2003 Park et al. ..................... 423/49

* cited by examiner

Primary Examiner—Porfirio Nazario-Gonzalez
(74) Attorney, Agent, or Firm—Bachman & LaPointe, P.C.

(57) ABSTRACT

Disclosed is a method of preparing a rhenium complex by use of a borohydride exchange resin, including dissolving perrhenic acid in a solution containing ethylenediamine tetraacetate, mannitol and stannous chloride to obtain a perrhenic acid solution (step 1), which is then mixed with disulfide in the presence of a borohydride exchange resin and reacts at room temperature, to obtain a rhenium complex (step 2). The preparation method of the current invention is characterized in that rhenium is reduced to have a desired oxidation number through the dissolving of the step 1, whereby the reaction of the step 2 can occur at room temperature. In addition, use of the borohydride exchange resin as a reducing agent results in direct formation of the rhenium complex of sulfide from disulfide, without the need of synthesis of thiol-protected S-precursor. Therefore, radioactive pharmaceuticals having high values can be economically and efficiently produced.

5 Claims, 6 Drawing Sheets

METHOD OF PREPARING RHENIUM COMPLEX USING BOROHYDRIDE EXCHANGE RESIN

BACKGROUND OF THE INVENTION

1. Field of the Invention

The present invention relates to preparation methods of rhenium complexes, and more specifically, to a method of preparing a rhenium complex by use of a borohydride exchange resin.

2. Description of the Related Art

In general, rhenium having isotopes of rhenium-186 ($^{186}$Re) and rhenium-188 ($^{188}$Re) belongs to the same group on the periodic table, together with technetium, and functions as a beta emitter for therapy and a gamma emitter for imaging at the same time. Practically, rhenium-186 or rhenium-188 has been utilized as radioactive pharmaceuticals applicable for palliating bone pain caused by secondary bone metastasis of prostatic cancer, lung cancer, breast cancer or the like.

Preparation methods of rhenium complex useful as radioactive pharmaceuticals include the formation of a rhenium-ligand complex, and then the labeling of a target compound through ligand substitution reaction.

Specifically, the rhenium complex results from the reaction of perrhenic acid with a reducing agent at a low pH, to obtain reduced rhenium, which then reacts with a ligand at high temperatures.

In this regard, S. Prakash et al. discloses that $NH_4ReO_4$ is mixed with aqueous ethylenediamine solution and $SnCl_2 \cdot 2H_2O$, and then heated for 30 min in a nitrogen atmosphere to prepare a desired rhenium complex [S. Prakash et al., Nuclear Medicine & Biology, Vol. 23, pp543–549, 1996].

Further, Jeong Jae-Min et al. discloses that $^{188}$Re-perrhenate eluate is added to a vial containing 2,2,9,9-tetramethyl-4,7-diaza-1,10-decanedithiol (TDD), $SnCl_2 \cdot 2H_2O$ and tartaric acid, and then boiled for 30 min, to obtain Re-TDD complex (J. M. Jeong et al., Nuclear Medicine & Biology, Vol 28, pp197–204, 2001].

Furthermore, S. Guhlke et al. discloses that $^{188}$Re-perrhenate eluate is added to a vial containing Bz-MAG$_3$-DH-Boc solution, K,Na-tartrate solution, $SnCl_2 \cdot 2H_2O$ and hydrochloric acid, pH about 3.8, after which a heating process is performed at 90° C. for 1 hour, to obtain $^{188}$Re-MAG$_3$-DH-Boc complex [S. Guhlke et al., Nuclear Medicine & Biology, Vol 25, pp621–631, 1998].

Like these, as for the formation of the complex through reaction of perrhenic acid with the ligand, the reduction of rhenium using the reducing agent should be preceded.

In such cases, the reduction is carried out by means of electrolysis or using the reducing agent, such as stannous chloride dehydrate ($SnCl_2 \cdot 2H_2O$), ferrous ion, ferrous-ascobate, formamidinesulfinic acid, sodium borohydride, etc. In common, use of stannous chloride dehydrate is preferable.

Although being stable under acidic conditions, stannous chloride dehydrate forms a precipitate under basic conditions. Whereas, sodium borohydride is stable under basic conditions, however becomes unstable under acidic conditions. Further, excessive use of the above reducing agent in the form of aqueous solution leads to the production of impurities, such as colloids, and residual toxicity. Thus, limitations are imposed on the use of predetermined amounts or more of the above reducing agent.

Moreover, in the above preparations, heat treatment should be performed to reduce rhenium or to react the reduced rhenium with the ligand. In this case, the heat treatment is carried out under nitrogen atmosphere to maintain a reduction atmosphere. However, such a high temperature reaction may cause the deterioration of antibodies and proteins bonded to the ligand, and also, may cleave chemical bonds. Therefore, antibodies and proteins weak against heat cannot be used. In addition, manufacturers have difficulties in controlling conditions of a refluxing process for use in treatment of radioactive materials at high temperatures.

SUMMARY OF THE INVENTION

Accordingly, it is an object of the present invention to alleviate the problems in the related art and to provide a method of preparing a rhenium complex, characterized in that a reaction can take place at room temperature, and a rhenium complex of sulfide can be directly formed from disulfide without the need of synthesizing a thiol-protected S-precursor.

To achieve the above object, the present invention provides a method of preparing a rhenium complex, including dissolving perrhenic acid in a solution containing ethylenediamine tetraacetate, mannitol and stannous chloride, to form a perrhenic acid solution (step 1); and mixing the perrhenic acid solution with disulfide in the presence of a borohydride exchange resin, followed by reaction, to obtain a rhenium complex (step 2).

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

Based on the present invention, a rhenium complex is prepared by dissolving perrhenic acid in a solution containing ethylenediamine tetraacetate, mannitol and stannous chloride to obtain a perrhenic acid solution (step 1), which is then mixed with disulfide in the presence of a borohydride exchange resin, followed by reaction at room temperature (step 2).

At the step 1, perrhenic acid is dissolved in the solution which contains ethylenediamine tetraacetate, mannitol and stannous chloride, to prepare a rhenium-ethylenediamine acetate complex.

In such cases, the above solution containing ethylenediamine tetraacetate, mannitol and stannous chloride functions to reduce rhenium so as to have an oxidation number required for formation of the rhenium complex. Specifically, the oxidation number of rhenium is converted from +7 to +3. As for the above solution, a weight ratio of ethylenediamine tetraacetate to mannitol to stannous chloride is in a range of 3–7:3–7:0.5–2, and preferably, 5:5:1. If the weight ratio is slightly out of the above range, the rhenium-ethylenediamine acetate complex has a low labeling efficiency. Meanwhile, if the weight ratio is extremely out of the above range, it is impossible to form the rhenium-ethylenediamine acetate complex.

At the step 2, the perrhenic acid solution of the above step 1 is mixed with disulfide in the presence of the borohydride exchange resin, and then reacts at room temperature, to obtain the rhenium complex. Specifically, S—S bond of disulfide is broken in the presence of the borohydride exchange resin, and thus, disulfide is converted to sulfide, which is then combined with rhenium having a low oxidation number obtained at step 1, to prepare a sulfide-rhenium complex.

Such sulfide means that S—S bond present in disulfide is reduced. Disulfide is the general term for compounds having disulfide functionality, and includes all compounds having S—S bond in a molecule. Disulfide having disulfide functionality may be compounds having functional groups which does not affect the above reaction, for example, amine, carboxyl, isocyanate, alcohol, ester, halogen element, alkoxy, sulfonic acid, nitro, amide, nitrile, isonitrile, etc. There are exemplified disulfide with diamine group, disulfide with dicarboxyl group, disulfide with heterocyclic compound, or disulfide with dialcohol group. Preferably, disulfide is selected from the group consisting of compounds represented by Formals 1 and 2, below. When an amine group or an isocyanate group is substituted in the molecule, a lone pair thereof may participate in a coordinated bond.

Formula 1

Formula 2

On the other hand, used as a reducing agent in the present invention, the borohydride exchange resin enables the direct formation of the rhenium complex from disulfide. Such a borohydride exchange resin has a structure of borohydride ion ($BH_4^-$) bonded to a cation which is supported to a polymer. An example of the cation used for bonding of the borohydride ion includes quaternary ammonium functionality. The borohydride exchange resin is used in the amount capable of sufficiently reducing disulfide and perrhenic acid.

The exchange resin supported with the borohydride ion ($BH_4^-$) includes all anion exchange resins having quaternary ammonium functionality. Such an exchange resin is easily commercially available, and is exemplified by polystyrene, high density polyethylene, and Amberlite.

The borohydride exchange resin is stable in acidic or basic ranges, that is, almost pH ranges, and hence, is easily applicable to biomolecules. As well, upon administration, it may be easily removed by a filtering process.

Further, the reaction of the present invention can take place at room temperature, which is different from that of conventional preparation of rhenium complex. Conventionally, a mixture of disulfide and rhenic acid reacts at high temperatures, to obtain a rhenium-sulfide complex. Whereas, in the present invention, the rhenium-sulfide complex can be prepared even through the reaction at room temperature. Thereby, deterioration of antibodies or proteins attached to ligands, which is regarded as the problem of the high temperature reaction, can be prevented. Also, a chemical bond is prevented from cleavage, thus hardly generating side-reactions.

Moreover, the method of the present invention is not particularly limited for addition sequence of disulfide and the perrhenic acid solution.

That is, disulfide and the perrhenic acid solution may be added together to the borohydride exchange resin, or disulfide and perrhenic acid may be sequentially added thereto. Alternatively, the perrhenic acid solution may be added to a mixture of lyophilized disulfide and borohydride exchange resin.

A better understanding of the present invention may be obtained through the following examples which are set forth to illustrate, but are not to be construed as the limit of the present invention.

EXAMPLE 1

Preparation of Rhenium Complex

Step 1:

To a vial containing 10 mg of ethylenediamine tetraacetate, 10 mg of mannitol and 2 mg of stannous chloride, 4 ml of aqueous solution of [$^{188}$Re] sodium perrhenate (5–10 mCi) and 2 ml of 1N hydrochloric acid were added, and then completely dissolved with stirring for 15 min. At this time, a resultant reaction was a rhenium-ethylenediamine acetate complex.

Step 2:

All of or parts of the above complex was introduced into a vial containing 1 mg of 3,3,10,10-tetramethyl-1,2-dithia-5,8-diazacyclodecaine and 5 mg of borohydride exchange resin, and mixed well and then reacted at room temperature for 3 hours. Thereafter, a filtering process using a membrane filter (0.22 μm) was performed, to prepare a rhenium-labeled sulfide.

COMPARATIVE EXAMPLE 1

Preparation of Rhenium Complex 4 ml of aqueous solution of ($^{188}$Re] sodium perrhenate (10 mCi) was introduced into a vial containing 1 mg of 3,3,10,10-tetramethyl-1,2-dithia-5,8-diazacyclodecaine and 1 mg of borohydride exchange resin, followed by mixing well and then reacting at room temperature for 3 hours. Thereafter, resultant reaction was filtered with a membrane filter (0.22 μm), to prepare a rhenium-labeled sulfide.

EXPERIMENTAL EXAMPLE 1

Measurement of Labeling Efficiency of Rhenium-Ethylenediamine Acetate Complex 1

The rhenium-ethylenediamine acetate complex prepared in Step 1 of Example 1 was measured for labeling efficiency by use of thin-layer chromatography. As such, conditions were acetone and distilled water.

Figure 1A:
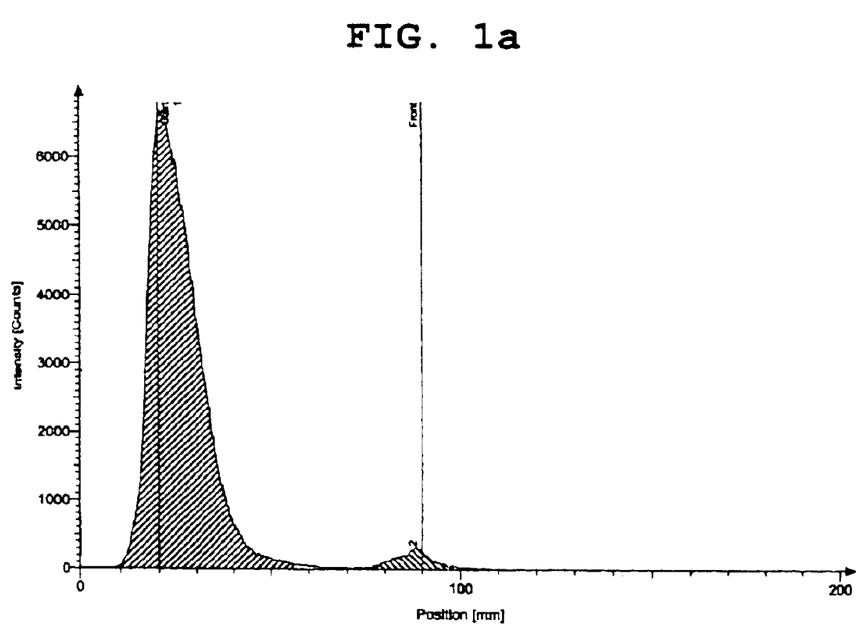
FIG. 1a is a graph showing labeling efficiency of a rhenium-ethylenediamine acetate complex prepared in Step 1 of Example 1 of the present invention, by means of thin-layer chromatography using acetone as a developing solvent.
Figure 1B:
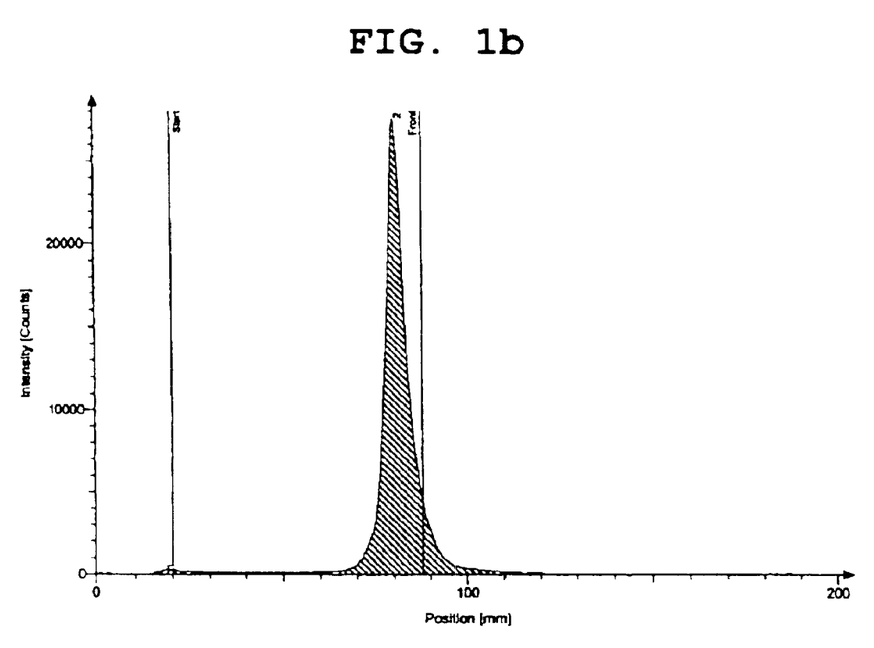
FIG. 1b is a graph showing labeling efficiency of the rhenium-ethylenediamine acetate complex prepared in Step 1 of Example 1 of the present invention, by means of thin-layer chromatography using distilled water as a developing solvent.

The results are shown in FIGS. 1a and 1b. Specifically, FIG. 1a shows the measurement result of thin-layer chromatography using acetone as a developing solvent, and FIG. 1b shows the measurement result of thin-layer chromatography using distilled water as a developing solvent.

As apparent from FIGS. 1a and 1b, the rhenium-ethylenediamine acetate complex prepared in Step 1 of Example 1 is confirmed to have labeling efficiency of 95% or more.

EXPERIMENTAL EXAMPLE 2

Measurement of Labeling Efficiency of Rhenium-Ethylenediamine Acetate Complex 2

The rhenium-ethylenediamine acetate complex prepared in Step 1 of Example 1 was measured for labeling efficiency using high performance liquid chromatography. In this case, a methanol/triethylammoniumphosphate buffer was used as a mobile phase, and a flow rate was maintained at 1 ml/min.

Figure 2:
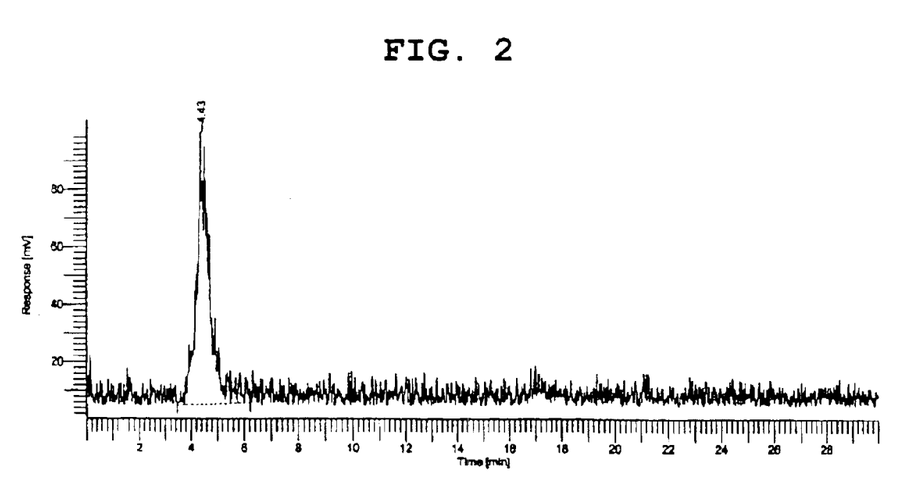
FIG. 2 is a graph showing labeling efficiency of the rhenium-ethylenediamine acetate complex prepared in Step 1 of Example 1 of the present invention, by means of high performance liquid chromatography.

The results are depicted in FIG. 2.

In FIG. 2, it can be seen that a peak observed at retention time of 3.8 min corresponds to rhenium-ethylenediamine tetraacetate. From this, the rhenium-ethylenediamine tetraacetate complex is confirmed to be prepared.

EXPERIMENTAL EXAMPLE 3

Measurement of Labeling Efficiency of Rhenium Complex 1

The rhenium complex prepared in Step 2 of Example 1 was measured for labeling efficiency using high performance liquid chromatography. At this time, a methanol/triethylammoniumphosphate buffer was used as a mobile phase, and a flow rate was maintained at 1 ml/min. In addition, for control, the end product of Comparative Example 1 was measured for labeling efficiency in the same manner as in the above procedure.

Figure 3:
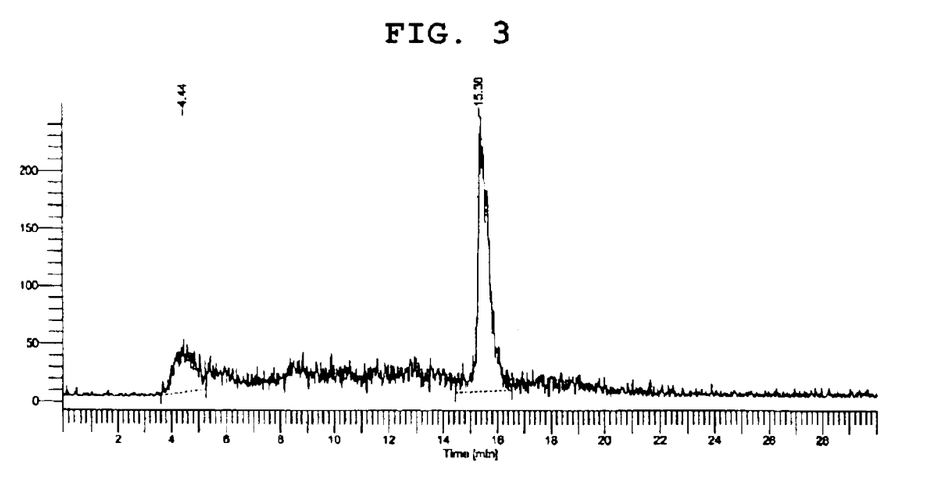
FIG. 3 is a graph showing labeling efficiency of a rhenium complex prepared in Step 2 of Example 1 of the present invention, by means of high performance liquid chromatography.

The results are depicted in FIG. 3.

Of two peaks observed in FIG. 3, one peak shown at retention time of 3.8 min corresponds to rhenium-ethylenediamine tetraacetate or perrhenate ion, and the other peak shown at retention time of 14.5 min corresponds to a target compound. From the results, the target compound having labeling efficiency of 77% or more is confirmed to be prepared.

However, it is noted that the end product of Comparative Example 1 is not labeled.

EXPERIMENTAL EXAMPLE 4

Measurement of Radiochemical Purity of Rhenium Complex

The rhenium complex prepared in Step 2 of Example 1 was isolated using high performance liquid chromatography. At this time, a methanol/triethylammoniumphosphate buffer was used as a mobile phase, and a flow rate was maintained at 1 ml/min.

Figure 4:
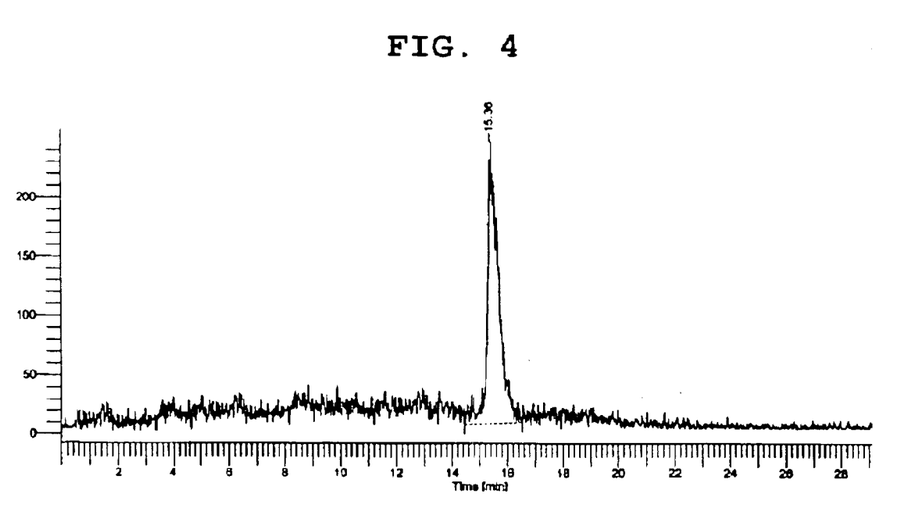
FIG. 4 is a graph showing radiochemical purity of the rhenium complex prepared in Step 2 of Example 1 of the present invention, by means of high performance liquid chromatography.

The results are represented in FIG. 4.

In FIG. 4, it is apparent that a peak observed at retention time of 14.5 min corresponds to a target compound. From this, the target compound having radiochemical purity of 99% or more is confirmed to be prepared.

EXPERIMENTAL EXAMPLE 5

Measurement of Labeling Efficiency of Rhenium Complex

The rhenium complex prepared in Step 2 of Example 1 was measured for labeling efficiency by use of thin-layer chromatography. As such, acetone and distilled water were used as a developing solvent, respectively.

Figure 5A:
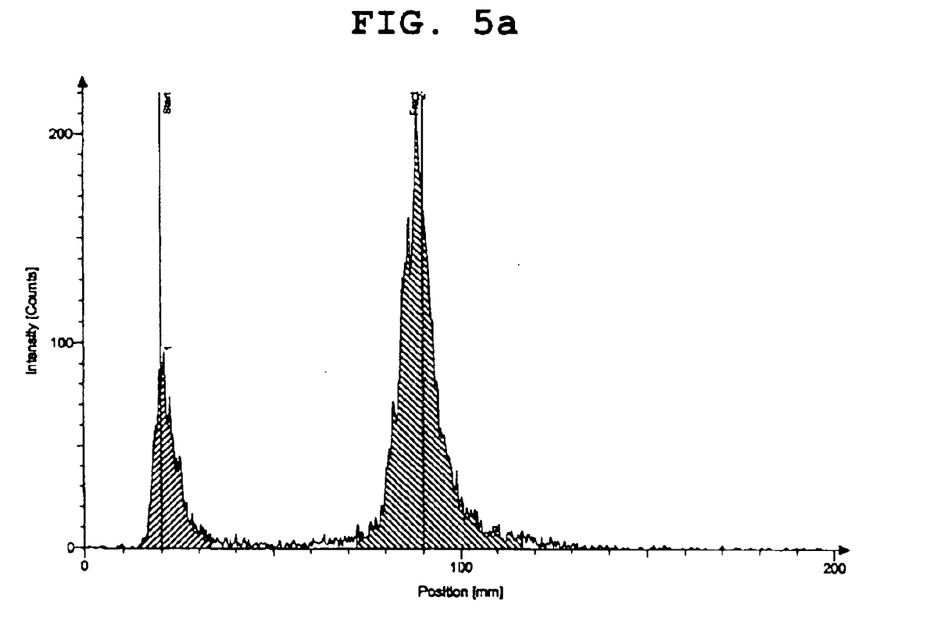
FIG. 5a is a graph showing labeling efficiency of the rhenium complex prepared in Step 2 of Example 1 of the present invention, by means of thin-layer chromatography using acetone as a developing solvent.
Figure 5B:
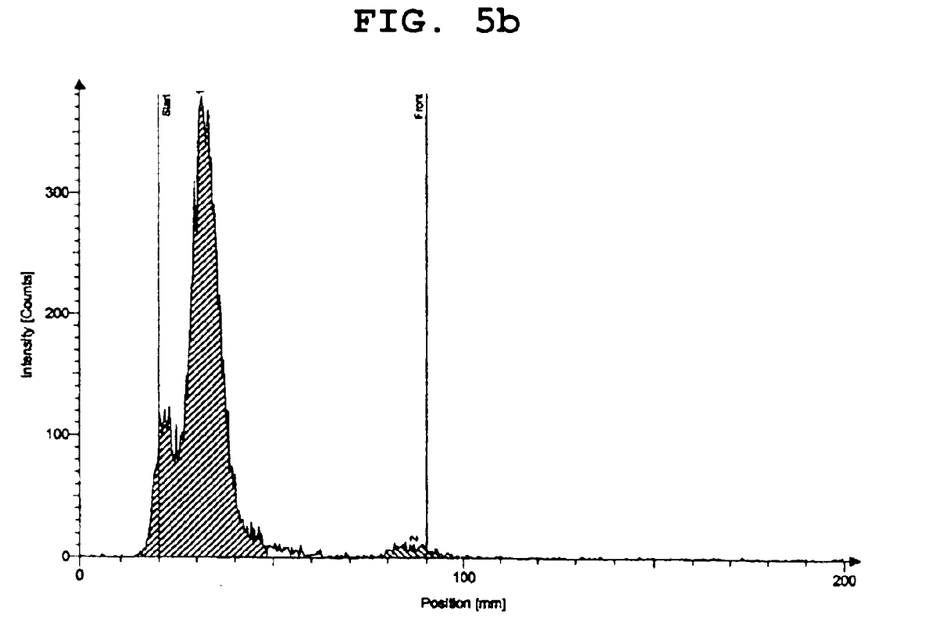
FIG. 5b is a graph showing labeling efficiency of the rhenium complex prepared in Step 2 of Example 1 of the present invention, by means of thin-layer chromatography using distilled water as a developing solvent.

The results are shown in FIGS. 5a and 5b. Specifically, FIG. 5a shows the measurement result of thin-layer chromatography using acetone as a developing solvent, and FIG. 5 shows the measurement result of thin-layer chromatography using distilled water as a developing solvent.

From FIGS. 5a and 5b, the labeling efficiency of the rhenium complex prepared in Step 2 of Example 1 can be seen.

As described above, the present invention provides a method of preparing a rhenium complex, characterized in that perrhenic acid is dissolved in a solution containing ethylenediamine tetraacetate, mannitol and stannous chloride, and thus, rhenium can be reduced to have a desired oxidation number. Thereby, a reaction of the following step can occur at room temperature. In addition, when a borohydride exchange resin is used as a reducing agent, the rhenium complex of sulfide can be directly obtained from disulfide, without the need of synthesis of thiol-protected S-precursor. Consequently, radioactive pharmaceuticals having high values can be economically and efficiently produced.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method of preparing a rhenium complex, comprising:

dissolving perrhenic acid in a solution containing ethylenediamine tetraacetate, mannitol and stannous chloride, to form a perrhenic acid solution (step 1); and mixing the perrhenic acid solution with disulfide in the presence of a borohydride exchange resin, followed by reaction, to obtain a rhenium complex (step 2).

2. The method according to claim 1, wherein a weight ratio of ethylenediamine tetraacetate to mannitol to stannous chloride is in a range of 3–7:3–7:0.5–2.

3. The method according to claim 1, wherein the disulfide comprises functionality of amine, carboxyl, isocyanate, alcohol, ester, halogen element, alkoxy, sulfonic acid, nitro, amide, nitrile, or isonitrile.

4. The method according to claim 3, wherein the disulfide is selected from the group consisting of compounds represented by Formulas 1 and 2, below:

Formula 1

Formula 2

-continued

-continued

5. The method according to claim 1, wherein the reaction of the step 2 takes place at room temperature.

* * * * *